(12) United States Patent
Bizub

(10) Patent No.: US 7,529,616 B2
(45) Date of Patent: May 5, 2009

(54) ANALYSIS OF FUEL COMBUSTION CHARACTERISTICS

(75) Inventor: Jeffrey Jacob Bizub, Milwaukee, WI (US)

(73) Assignee: Dresser, Inc., Addison, TX (US)

(*) Notice: Subject to any disclaimer, the term of this patent is extended or adjusted under 35 U.S.C. 154(b) by 428 days.

(21) Appl. No.: 11/390,942

(22) Filed: Mar. 28, 2006

(65) Prior Publication Data

US 2007/0239345 A1 Oct. 11, 2007

(51) Int. Cl.
*G06F 19/00* (2006.01)
*G01M 19/00* (2006.01)

(52) U.S. Cl. .................. 701/114; 73/118.01; 701/103; 701/111

(58) Field of Classification Search .................. 701/114, 701/111, 103–105, 115; 73/118.01; 123/478, 123/480, 299

See application file for complete search history.

(56) References Cited

U.S. PATENT DOCUMENTS

| | | | |
|---|---|---|---|
| 2,937,519 A | | 5/1960 | Brace et al. |
| 4,140,004 A | | 2/1979 | Smith et al. |
| 4,181,944 A | * | 1/1980 | Yamauchi et al. ........... 701/108 |
| 4,402,212 A | | 9/1983 | Childs |
| 4,677,559 A | * | 6/1987 | van Bruck .................. 701/109 |
| 5,586,537 A | | 12/1996 | Tomisawa et al. |
| 5,750,995 A | | 5/1998 | Clarke |
| 5,906,190 A | | 5/1999 | Hole et al. |
| 6,065,442 A | * | 5/2000 | Motose et al. ............... 123/294 |
| 6,286,482 B1 | | 9/2001 | Flynn et al. |
| 6,443,104 B1 | | 9/2002 | Simescu et al. |
| 6,474,308 B2 | | 11/2002 | Okumura et al. |
| 6,637,404 B2 | | 10/2003 | Fuerhapter et al. |
| 6,651,610 B2 | * | 11/2003 | Nishimura et al. .......... 123/295 |
| 6,763,799 B2 | * | 7/2004 | Ito et al. ..................... 123/299 |
| 2003/0052041 A1 | | 3/2003 | Erwin et al. |
| 2003/0145836 A1 | | 8/2003 | Linna et al. |
| 2004/0134450 A1 | | 7/2004 | Bauer et al. |
| 2004/0154386 A1 | | 8/2004 | Shinzawa |

FOREIGN PATENT DOCUMENTS

| | | |
|---|---|---|
| DE | 199 04 319 | 8/2000 |
| EP | 0 143 571 | 6/1985 |
| JP | 62282265 | 12/1987 |
| JP | 2001329905 | 11/2001 |
| JP | 2007-113485 A * | 5/2007 |

OTHER PUBLICATIONS

International Search Report and Written Opinion of the International Searching Authority issued in International Application No. PCT/US2007/006813; Sep. 6, 2007; 6 pages.

Wakisaka et al.; "Numerical Prediction of Mixture Formation and Combustion Processes in Premixed Compression Ignition Engines"; The Fifth International Symposium on Diagnostics and Modeling of Combustion in Internal Combustion Engines (COMODIA 2001); Jul. 1-4, 2001; Nagoya, Japan; pp. 426-433.

Advanced Engine Technology Ltd.; "Diesel Fuel Ignition Quality Tester (IQT)"; 4 pages.

* cited by examiner

*Primary Examiner*—Hieu T Vo
(74) *Attorney, Agent, or Firm*—Fish & Richardson P.C.

(57) ABSTRACT

Some embodiments of a system for determining combustion characteristics may be capable of automatically determining and displaying a plurality of combustion characteristics on a multiple-axis plot. In such embodiments, a single combustion test in the system's controlled combustion chamber may provide a user with automatic analysis and display of three, four, five, six, or more combustion characteristics.

27 Claims, 11 Drawing Sheets

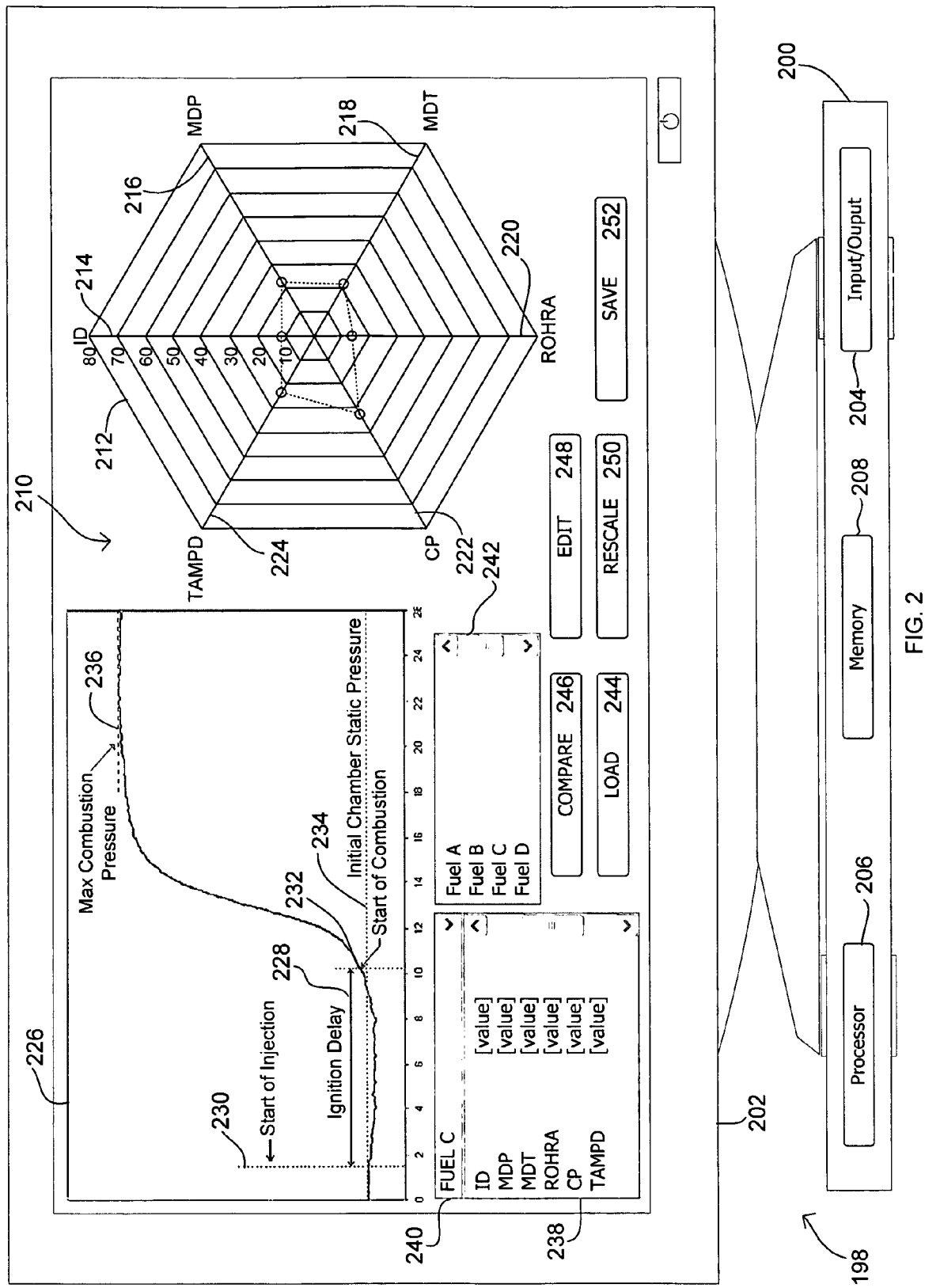

| Abbreviation | Unit of Measure | Fuel A value | Fuel B value | Fuel C value | Fuel D value | Scale 0-100 |
|---|---|---|---|---|---|---|
| TAMPD | Milliseconds | 5 ms / 10 scaled value | 8 ms / 16 scaled value | 24 ms / 48 scaled value | 2.16 ms / 4.32 scaled value | 20 ms = 0 / 0.5 ms = 100 |

ANALYSIS OF FUEL COMBUSTION CHARACTERISTICS

TECHNICAL FIELD

This document relates to determination and analysis of combustion characteristics of various fuels.

BACKGROUND

Some combustion characteristics of a fuel can be measured to predict the fuel's performance in a particular engine. For example, fuels that may be used in homogeneous charge compression ignition (HCCI) engines, including some diesel engines, are frequently analyzed to determine characteristics known as the cetane number and octane number. Such characteristics have previously been employed in an attempt to aid an engine designer in determining the proper fuel mixture for use in a particular HCCI engine.

The octane number can be an indication of a fuel's resistance to detonation. For example, a fuel having a high octane number will resist auto-ignition more than another fuel having a lower octane number. The uncontrolled auto-ignition of a fuel in an engine is undesirable because it leads to a phenomenon known as engine knock. A forceful knock is usually accompanied by rapid build up of pressure and vibration that can damage the engine.

The cetane number can be an indication of a fuel's propensity to auto-ignite. As such, the cetane number may affect an engine's ability to cold start, may affect the engine's emissions, and may affect the engine's combustion efficiency. For example, in a typical diesel engine, the fuel is ignited by hot air (e.g., heated by compression). The fuel is usually injected into this hot air just before the piston reaches top-center position, and in most designs, ignition should begin just as the piston reaches this position. If the fuel does not ignite when the piston is at the top-center position, the entire charge of fuel may become thoroughly mixed with air, thereby causing a steeper pressure rise when the fuel finally does ignite. Accordingly, a diesel engine that operates with a fuel having a lower-than-recommended cetane number may be difficult to start, may be generally more noisy, may operate roughly, and may have higher emissions.

Because the octane number and cetane number of a particular fuel may indicate opposite characteristics, it is usually the case that a higher cetane number results in a lower the octane number, and vice versa. Traditionally, an engine designer was required to test various fuel mixtures to determine individual cetane numbers or octane numbers and to subsequently select a fuel having a desirable compromise of the cetane number and the octane number for use in a particular engine. In some circumstances, these characteristics (cetane number or octane number) by themselves are not an adequate indicator of the fuel's performance in particular engines, including some HCCI engines that utilize blends of octane and cetane fuels.

SUMMARY

Some embodiments of a system for determining combustion characteristics may be capable of automatically determining and displaying a plurality of combustion characteristics on a multiple-axis plot. In such embodiments, a single combustion test in the system's controlled combustion chamber may provide a user with automatic analysis and display of three, four, five, six, or more combustion characteristics. For example, the system may be capable of automatically analyzing and displaying a number of combustion characteristics including ignition delay, maximum combustion pressure, maximum combustion temperature, rate of heat release, combustion period, and the time at which the maximum pressure developed. In these circumstances, a user may view a single plot or other displayed report to readily gather resourceful information regarding a particular fuel's combustion characteristics.

In some embodiments, a method for determining the operability of a fuel in an engine may include identifying values for at least three combustion characteristics of a tested fuel. The at least three combustion characteristics may be selected from the group consisting of ignition delay, maximum delta pressure, maximum delta temperature, rate of heat release area, combustion period, and time at which the maximum pressure developed. The method may also include using the identified values to assess the suitability of the tested fuel for operation in an engine configuration.

In certain embodiments, a method for assessing combustion characteristics of a fuel, may include determining values for at least three combustion characteristics of a fuel. The at least three combustion characteristics may be selected from the group consisting of ignition delay, maximum delta pressure, maximum delta temperature, rate of heat release area, combustion period, and time at which the maximum pressure developed. The method may also include associating the determined values with the fuel.

In some embodiments, a method for assessing a combustion characteristic of a fuel may include determining a value for at least one combustion characteristic of a fuel selected from the group consisting of rate of heat release area and combustion period. The method may also include associating the determined value with the fuel.

In particular embodiments, a computer-implemented method of reporting combustion characteristics of a fuel may include receiving data indicative of pressure and temperature in a combustion chamber at a predetermined sample rate during combustion of a fuel in the combustion chamber. The method may also include determining values for a plurality of combustion characteristics associated with the fuel combusted in the combustion chamber. The plurality of combustion characteristics may be at least three of the characteristics selected from the group consisting of: ignition delay, maximum delta pressure, maximum delta temperature, rate of heat release area, combustion period, and time at which the maximum pressure developed. The method may further include generating an output report indicative of determined or scaled values of the at least three combustion characteristics. The output report may include the determined or scaled values of the at least three combustion characteristics displayed on a multiple-axis plot, and the multiple-axis plot may have an axis for each of the at least three combustion characteristics.

In some embodiments, a method of identifying combustion characteristics of a fuel may include initiating a computer system to determine values for a plurality of combustion characteristics associated with a first fuel combusted in the combustion chamber. The plurality of combustion characteristics may be at least three of the characteristics selected from the group consisting of: ignition delay, maximum combustion pressure, maximum combustion temperature, rate of heat release, combustion period, and time at which the maximum pressure developed. The method may also include causing the first fuel to be injected into a combustion chamber so that the first fuel combusts. The combustion chamber may include one or more sensors that are electrically coupled to the computer system. The method may further include viewing an output report generated by the computer system indicative of determined or scaled values of the at least three combustion characteristics. The output report may include a multiple-axis plot having an axis for each of the at least three combustion characteristics.

These and other embodiments may provide one or more of the following advantages. First, a plurality of combustion characteristics may be determined from a single combustion test. For example, a single combustion test may yield values for five or six combustion characteristics, which can be associated with the tested fuel to provide useful information for an engine designer or fuel developer. Second, the plurality of combustion characteristics may be displayed on a multiple-axis plot so that a user may readily gather useful information regarding a particular fuel by viewing an individual plot. For example, if the system analyzes six combustion characteristics (e.g., ignition delay, maximum combustion pressure, maximum combustion temperature, rate of heat release, combustion period, and the time at which the maximum pressure developed), a six-axis plot may be displayed so that each axis represents a value scale for an associated combustion characteristic. Thus, a user viewing the six-axis plot may readily gather useful information about the tested fuel from viewing the individual plot associated with the tested fuel, thereby saving time normally consumed by testing and analyzing fuel characteristics.

Third, the multiple-axis plot or other displayed report for communicating a plurality of combustion characteristics of a tested fuel may be used as a fuel form factor to readily analyze and compare various fuel mixtures. For example, if testing of a new engine design reveals that a first fuel mixture provides satisfactory engine performance at a cold temperature while a second fuel mixture provides satisfactory performance at a hot temperature, the engine designer may efficiently compare (e.g., side-by-side or overlaid) the multiple-axis plots associated with the first and second fuel mixtures to identify or categorize a range of desirable combustion characteristics. In this example, the engine designer may change the engine design (e.g., adjust the compression ratio, the piston position, or the like) so that one of the first and second fuel mixtures performs satisfactorily at both cold and hot temperatures. In addition or in the alternative, a user may develop a third fuel mixture that performs satisfactorily at both cold and hot temperatures, and such development may be based (at least in part) upon the knowledge gained from the quantitative or qualitative comparison of the multiple-axis plots associated with the first and second fuel mixtures. In some embodiments, the fuel form factor may be at least partially defined by the shape of the multiple-axis plot. In other embodiments, the fuel form factor may be at least partially defined by an area value of the shape of the multiple-axis plot such that different fuels may be distinguished by the different area values at particular ordinates.

Fourth, data from the multiple-axis plot may be input into an engine simulation system (e.g., implemented on a computer system or the like) to provide feedback for certain criteria of the fuel's combustion characteristics. Accordingly, the data from the multiple-axis plot may facilitate the design of a combustion engine or the design of a customized fuel in a known engine by permitting a designer to readily simulate one or more fuels in the engine simulation system.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 is a front view of a computer display of the system of FIG. 1.

Like reference symbols in the various drawings indicate like elements.

DETAILED DESCRIPTION OF ILLUSTRATIVE EMBODIMENTS

Figure 1:
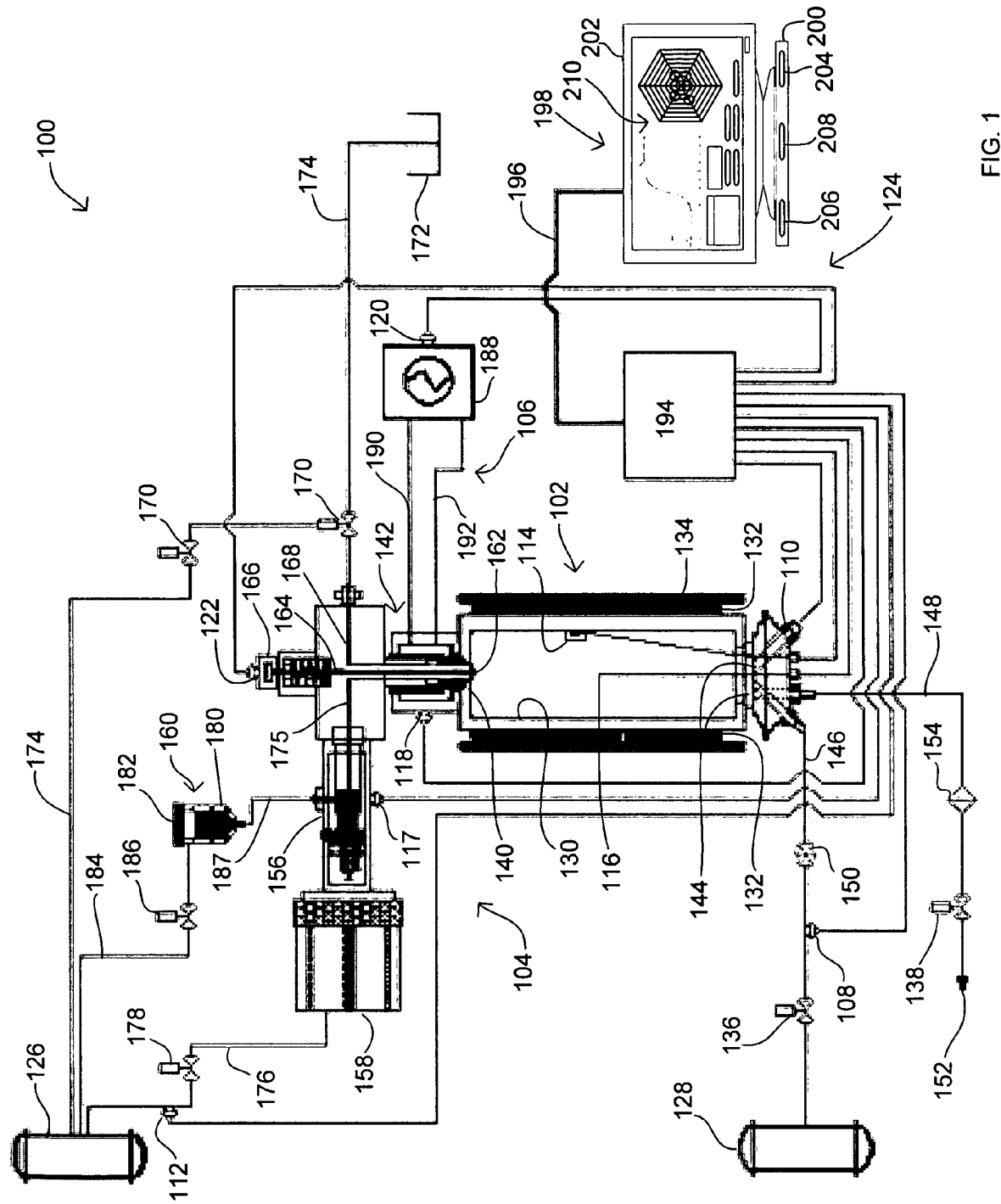
FIG. 1 is a schematic of an analytical measurement system in accordance with some embodiments of the invention.

Referring to FIG. 1, an analytical measurement system 100 may include a combustion chamber 102 and a fuel injection system 104. In this embodiment, the combustion chamber 102 may comprise a constant volume combustion chamber that receives a fuel specimen from the injection system 104. Other embodiments may include a variable volume combustion chamber. The system may also include a plurality of instrument sensors 108, 110, 112, 114, 116, 117, 118, 120, and 122 that are configured to communicate with a control system 124. In addition, the system may include a coolant system 106 and one or more compressed gas pressure supplies 126 and 128.

The analytical measurement system 100 may be used to determine a plurality of combustion characteristics of a tested fuel, such as the ignition delay (ID), maximum delta pressure (MDP), maximum delta temperature (MDT), rate of heat release area (ROHRA), combustion period (CP), time at maximum pressure developed (TAMPD), or the like. In this embodiment, the combustion characteristics may be determined by the analytical measurement system 100 using data from one or more sensors 108, 110, 112, 114, 116, 117, 118, 120, and 122 that measure pressures, temperatures, or other parameters when a fuel specimen is combusted in the combustion chamber 102. In some embodiments, the combustion chamber 102 may be used to simulate the conditions of a combustion process of an HCCI engine, such as an actual or prototypical diesel engine. The data output from the sensors 108, 110, 112, 114, 116, 117, 118, 120, and 122 may be received by the control system 124 for determination (e.g., direct measurement by the sensor, computational algorithm, statistical calculation, mathematical conversion or derivation, other determinative techniques, or a combination thereof) of the combustion characteristics.

The combustion chamber 102 may include a cylindrical block 130 having a substantially constant volume. In this embodiment, for example, the substantially constant volume of the cylindrical block may be 0.60±0.03 L. Additionally, the combustion chamber 102 may include a plurality of external heating elements 132, a heat shield 134, an intake valve 136, and an exhaust valve 138. An opening 140 at a first end of the combustion chamber 102 may accommodate the insertion of a fuel injector nozzle assembly 142, and a plurality of openings 144 at a second end of the combustion chamber 102 may accommodate the insertion of the intake air line 146, the exhaust air line 148, and a plurality of sensors 110, 114, and 116.

In this embodiment, one end of the intake air line 146 may be in fluid communication with one of the openings 144 at the bottom of the combustion chamber 102, and the opposite end of the intake air line 146 may be in fluid communication with the charge air supply 128. The intake air line 146 may supply the charge air supply to the combustion chamber 102 before the combustion event (described in more detail below). The input of intake air to the combustion chamber 102 may be controlled by the intake valve 136, which in some embodiments, may be electronically actuated, may meter the intake air, or both. Additionally, the intake air line 146 may include a safety valve 150 that acts as a backup in the event of a failure of the intake valve 136. The supply of compressed gas from the charge air supply 128 may be regulated by a regulator. In one instance, the regulator is two-stage regulator capable of controlling the pressure of the intake air to a minimum pressure of, for example, about 2.40 MPa. However, other single or multi stage regulators, as well as lesser or greater minimum pressures, are within the scope of the invention.

Still referring to FIG. 1, one end of the exhaust air line 148 may be in fluid communication with one of the openings 144 at the bottom of the combustion chamber 102, and the opposite end of the exhaust air line 148 may be in fluid communication with an exhaust ventilation system 152. The exhaust air line 148 may discharge the byproducts of the combustion process from the combustion chamber 102. The discharge of the byproducts of the combustion process from the combustion chamber 102 may be controlled by the exhaust valve 138, which in some embodiments, may be electronically actuated. The exhaust air line 148 may contain an inline filter 154 that partially filters the byproducts of the combustion process.

The fuel injection system 104 may include a fuel injection pump 156, an injector pump actuator 158, the previously described fuel injector nozzle assembly 142, and a fuel sample reservoir 160. In such circumstances, the fuel injection system 104 may be controlled to deliver a fuel specimen from the reservoir 160 to the combustion chamber (e.g., via the nozzle assembly 142).

The fuel injector nozzle assembly 142 may include a fuel injector nozzle 162, such as a standard one-hole nozzle or a standard multiple-hole nozzle. The fuel injector nozzle 162 may incorporate a spring-loaded needle extension 164 that includes a screw and lock nut 166 for adjusting the fuel injector nozzle 162 opening pressure setting. Further, the fuel injector nozzle assembly 142 may include a fuel bleed passage 168 that allows for fluid communication with one or more external bleed valves 170 (for bleeding fuel from the fuel injector nozzle assembly 142). The external bleed valves 170 may be in fluid communication with a sample waste drain 172 via a drain line 174. The fuel injector nozzle assembly 142 may include an injection nozzle motion sensor 122 mounted near the top of the spring-loaded needle extension 164. The injection nozzle motion sensor 122 may be used to determine when the spring-loaded needle extension 164 lifts, thereby allowing the control system 124 to determine the start, the end, and the duration of a fuel injection period.

The fuel injector nozzle assembly 142 may be coupled to the fuel injection pump 156. The fuel injection pump 156 may supply fuel to the fuel injector nozzle assembly 142 via an internal fuel supply passage 175. In some embodiments, the fuel injection system 104 of the analytical measurement system 100 may be pneumatically actuated. To this end, the fuel injection pump 156 may be coupled to the injector pump actuator 158, which may be in fluid communication with the pneumatic air supply 126 via a pneumatic air supply line 176. The supply of compressed air from the pneumatic air supply 126 to the injector pump actuator 158 may be regulated by a regulator switch gauge 112. In this embodiment, the regulator switch gauge 112 may be a two-stage regulator capable of controlling the downstream pressure to a minimum pressure of, for example, about 0.75 MPa. Use of single or multi stage regulators, as well as lesser or greater minimum pressures, are within the scope of the invention. As such, the supply of compressed air from the pneumatic air supply 126 to the injector pump actuator 158 (controlled by an actuator valve 178) causes the mechanical action of the injector pump actuator 158 on the fuel injection pump 156. In other embodiments, the fuel injection system can be actuated using wholly or partially hydraulic or electric systems.

Still referring to FIG. 1, the fuel sample reservoir 160 may have a substantially fixed volume, for example, about 100 mL. The reservoir 160 may comprise a reservoir body 180 and a reservoir top 182 that can be removably attached via a threaded, snap, or bolt connection. The reservoir 160 may be in fluid communication with the pneumatic air supply 126 via a pneumatic air supply line 184. The supply of compressed air from the pneumatic air supply 126 to the reservoir 160 may be regulated by reservoir valve 186. The reservoir 160 may be in fluid communication with the fuel injection pump 156 via fuel supply line 187.

The coolant system 106 may comprise a closed-loop circulating coolant system to control the temperature of the fuel injector nozzle 162. The coolant system 106 may include an auxiliary heat exchanger 188 with a built-in circulating pump and flow control valves to control the flow of coolant. The coolant may flow between the auxiliary heat exchanger 188 and the fuel injector nozzle 162 via coolant supply line 190 and coolant return line 192. The coolant fluid may comprise water, an ethylene glycol-based antifreeze, a mix of water and an ethylene glycol-based antifreeze (e.g., 50:50 ratio by volume), or the like.

As shown in FIG. 1, the analytical measurement system 100 may include a plurality of sensors 108, 110, 112, 114, 116, 117, 118, 120, and 122. In this embodiment, at least some of the sensors 108, 110, 112, 114, 116, 117, 118, 120, and 122 may be used to measure a parameter such as pressure, temperature, or another condition within the analytical measurement system 100. For example, the sensors may include a static pressure sensor 108, a dynamic pressure sensor 110, an injection pressure gauge 112, an inner wall temperature sensor 114, a charge air temperature sensor 116, a fuel injection temperature sensor 117, an injector nozzle temperature sensor 118, a coolant system sensor 120 and an injector nozzle motion sensor 122.

The static pressure sensor 108 may be a pressure transducer that is installed to detect the static pressure within the combustion chamber 102 before and after each combustion cycle. The dynamic pressure sensor 110 may also be a pressure transducer. The dynamic pressure sensor 110 may be configured to detect the pressure within the combustion chamber at a predetermined sample rate during each combustion cycle. For example, the sample rate of the dynamic pressure sensor 110 may be 0.2 ms or less, may be 0.1 ms or less, and may be approximately 0.05 ms, and the sample events may occur for a duration of about 100 ms. In some embodiments, the dynamic pressure sensor 110 may include an integrated temperature sensor to contemporaneously detect the temperature within the combustion chamber 102.

The injection pressure gauge 112 may be a calibrated pressure regulator installed between the pneumatic air supply 126 and the fuel injection pump actuator 158. In this embodiment the injection pressure regulator gauge 112 is configured to monitor and regulate the air pressure in the pneumatic air supply line 176.

The inner wall temperature sensor 114 may be a thermocouple, such as a type K thermocouple with stainless steel sheath, which can be fastened to the inner surface of the cylindrical block 130. The inner wall temperature sensor 114 may be configured to monitor the temperature of the inner surface of the cylindrical block 130.

The charge air temperature sensor 116 may also be a thermocouple, such as a type K thermocouple with stainless steel sheath, which can be inserted into the interior space of the combustion chamber 102. The charge air temperature sensor 116 may be configured to monitor the temperature within the combustion chamber 102 before, during, and after the combustion process.

In this embodiment, the fuel injection temperature sensor 117 may be a platinum resistance thermometer with a stainless steel sheath, which can be inserted into the fuel injection pump 156. In such circumstances, the fuel injector temperature sensor 117 may be capable of detecting the temperature of the fuel injection pump 156. Also in this embodiment, the injector nozzle temperature sensor 118 may be a platinum resistance thermometer with a stainless steel sheath, which can be inserted in the fuel injector nozzle assembly 142 to detect the temperature of the fuel injector nozzle 162. The coolant temperature sensor 120 may be an external sensor that can be used to detect the temperature of the coolant at the auxiliary heat exchanger 188. The injector nozzle motion sensor 122 may be configured to provide a suitable gap between the sensing surface and the end of the spring-loaded needle extension 164. Such a configuration allows the sensor 122 to detect the start of fuel injection and the end of fuel injection, and this data may be used by the control system 124 to calculate the duration of the fuel injection period.

The sensors 108, 110, 112, 114, 116, 117, 118, 120, and 122 may interface with the control system 124 via a controller card 194 or the like. In this embodiment, the controller card 194 may comprise a controller circuit and may be connected via a cable 196, such as a USB cable, to a computer system 198. Alternatively, the controller card 194 may be directly installed into the computer system 198. In some embodiments, the computer 198 may comprise a personal computer system having a computer housing 200 and a display device 202. The computer housing 200 may comprise an input/output interface 204, a processor 206, and computer memory 208 (e.g., a computer-readable medium such as semiconductor memory devices, flash memory devices, magnetic disks including internal hard disks or removable disks, or magneto-optical disks) so as to provide automated control of particular combustion analysis components. For example, the processor 206 may be configured to execute a computer software code stored on the memory 208 so that, when executed, the computer software code may receive data from the sensors, process such data, and generate an output report 210 that displays a plurality of combustion characteristics on the display device 202. The output report 210 may be saved in the computer memory 208 as well as displayed on the display device 202.

Referring to FIG. 2, the computer system 198 may provide a user with an output report 210 that contemporaneously displays values for a plurality of combustion characteristics. In this embodiment, the output report 210 comprises a multiple-axis plot 212 showing values for six combustion characteristics: ID, MDP, MDP, ROHRA, CP, and TAMPD. For example, the value for the ID (ignition delay) combustion characteristic may be plotted on the ID axis 214. Likewise, the value for the MDP (maximum delta pressure) combustion characteristic may be plotted on the MDP axis 216, the value for the MDT (maximum delta temperature) combustion characteristic may be plotted on the MDT axis 218, the value for the ROHRA (rate of heat release area) combustion characteristic may be plotted on the ROHRA axis 220, the value for the CP (combustion period) combustion characteristic may be plotted on the CP axis 222, and the value for the TAMPD (time at maximum pressure developed) combustion characteristic may be plotted on the TAMPD axis 224. The multiple-axis plot 212 may include a line (e.g., a dotted line in this embodiment shown in FIG. 2) connecting the value points on each axis, thereby providing a shape that may be different for each tested fuel depending upon the combustion characteristics of the fuels. The resultant multiple-axis plot 212 may serve as a fuel form factor that can be used to quantitatively or qualitatively describe the combustion characteristics of one or more fuel.

It should be understood that the multiple-axis plot 212 may show values for a number of combustion characteristics other than six characteristics. For example, in some embodiments, the multiple-axis plot 212 may show a set of three combustion characteristics (e.g., sets of three such as ID, ROHRA, and TAMPD; ID, MDP, and CP; or the like). In another example, the multiple-axis plot 212 may show two, three, four, five or more combustion characteristics. In such circumstances, the multiple-axis plot may comprise an axis for each of the selected combustion characteristics. The system 100 and control system 124 (FIG. 1) can be configured to determine at least the selected combustion characteristics. Furthermore, it should be understood that the multiple-axis plot 212 or other portion of the output report 210 may additionally or alternatively show values for combustion characteristics other than the previously described ID, MDP, MDP, ROHRA, CP, and TAMPD characteristics. For example, in some embodiments, the multiple-axis plot 212 may show values for combustion characteristics such as cetane number, octane number, aromatic content, or the like in addition to one or more values of ID, MDP, MDP, ROHRA, CP, and TAMPD characteristics. If desired, the system 100 and control system 124 (FIG. 1) can be configured to determine these alternate combustion characteristics.

In some embodiments, the output report 210 displayed on the display device 202 may show a pressure trace plot 226 which is indicative of the data from the dynamic pressure sensor 110 in the combustion chamber 102 before and during a combustion event. The pressure trace plot 226 may be used to graphically view the ignition delay 228 of the combustion event. In this embodiment the ignition delay 228 may be defined as the approximate time from the start of injection 230 to the start of combustion 232 (the start of combustion 232 may be determined from a detected change in pressure over the initial combustion chamber static pressure 234 in the combustion chamber 102 created by the start of a combustion event). Further, the pressure trace plot 226 may be used to graphically view the maximum combustion pressure 236 created by the combustion cycle. It should be understood that in addition to or in alternative to displaying the pressure trace plot 226, the output report 210 may display a temperature trace plot (e.g., indicative of the data from the charge air temperature sensor 116 before and during the combustion event), a derivative pressure trace plot (e.g., derived from the data from the dynamic pressure sensor 110 before and during the combustion event), or the like.

Still referring to FIG. 2, the output report 210 displayed on the display device 202 may also show a numeric display area 238 that displays the values of the combustion characteristics (e.g., ID, MDP, MDP, ROHRA, CP, and TAMPD) determined by the analytical measurement system 100. By selecting a previously tested fuel (for example Fuel A, Fuel B, Fuel C, or Fuel D) from a drop down menu 240, the combustion characteristics of different fuels may be alternately displayed in the numeric display area 238 and in the multiple-axis plot 212.

The previously determined combustion characteristics of one or more fuel(s) may be displayed separately or contemporaneously in the multiple-axis plot 212 using a fuel display box 242. One or more of the fuels may be selected in the fuel display box 242 (e.g., by a user clicking the fuel names with a mouse or other input device). By selecting a load button 244, the computer 198 loads the selected output report(s) from memory 208. Further, by selecting a compare button 246, the computer 198 generates an output report 210 that is displayed on the display device 202. The output report 210 includes a plot of the combustion characteristics of the one or more selected fuel samples on the multiple-axis plot 212. Further, the display device 202 may contemporaneously show the pressure trace plots 226 for each of the one or more selected fuel samples.

In this embodiment, selecting an edit button 248 allows for the source data in the output report 210 to be edited. In addition or in the alternative, the edit button 248 may permit a user to edit axis labels, the plot title, the line titles, the line colors, the orientation of the plot, the arrangement of the axes in the plot, and other such edits. Selecting a rescale button 250 allows the multiple-axis plot 212 or the pressure trace plot 226 to be rescaled. The plots may be rescaled to a best-fit scale, a user defined scale, or the like. Additionally, a save button 252 may allow the output report 210 and other data currently displayed on the monitor 202 to be saved in memory 208.

Figure 3A:
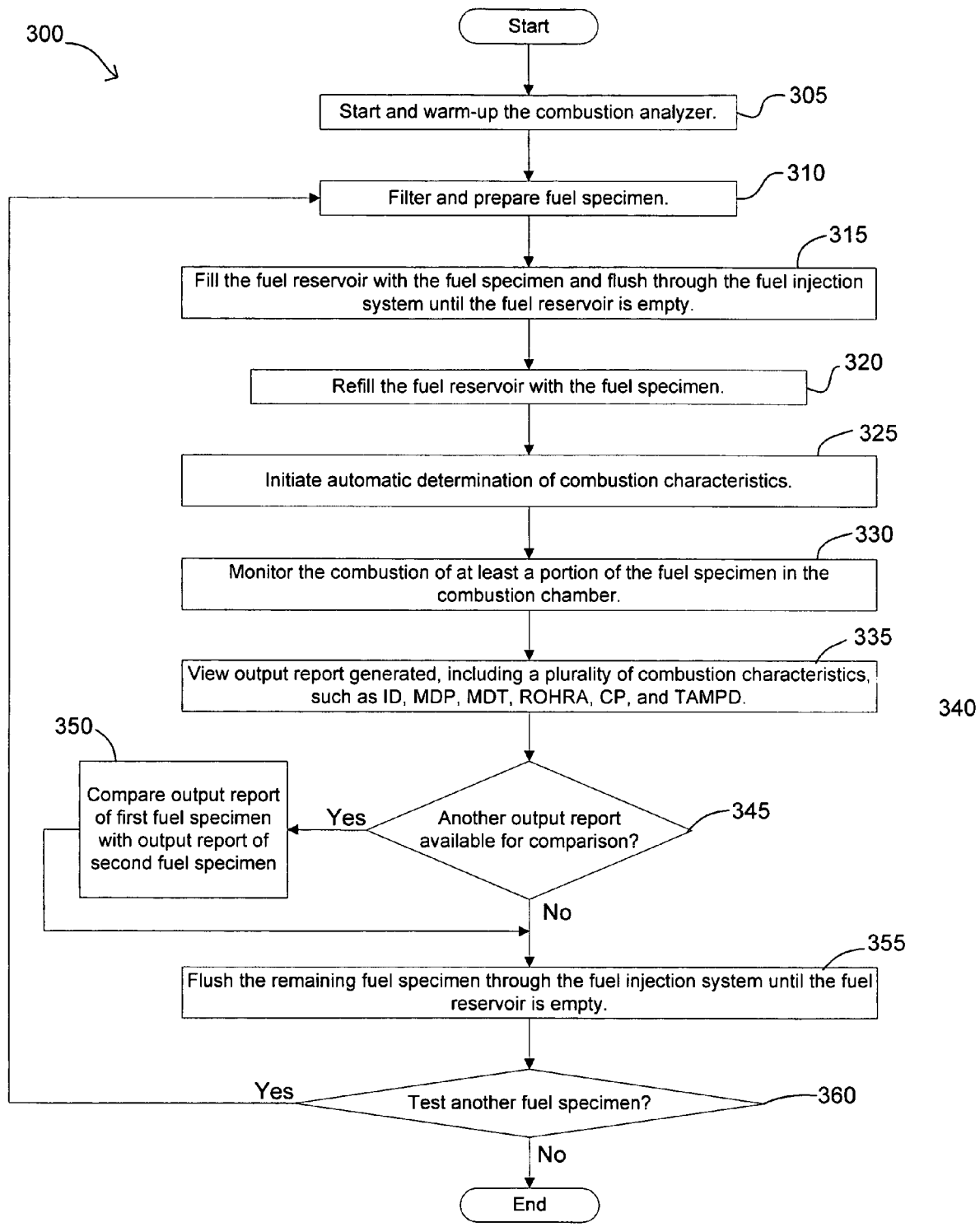
FIG. 3A is a flowchart showing a method for determining combustion characteristics of a fuel in accordance with some embodiments.

Referring to FIG. 3A, one exemplary method 300 of determining the combustion characteristics of a tested fuel may include the operation 305 of starting and warming-up the combustion chamber 102. For example, the charge air valve 136 (FIG. 1) at the source of the charge air supply 128 may be opened so as to fill the combustion chamber 102 with air. The charge air supply pressure regulators (not shown in FIG. 1) may be adjusted as needed to provide the combustion chamber 102 static air pressure, for example, at about 2.4 MPa+/−0.02 MPa. In this embodiment of the method 300, the combustion chamber 102 may be filled with air that comprises a mixture of about 20.9% Oxygen, about 78-79% Nitrogen, and smaller percentages of other gases found in the atmosphere. As part of the starting and warming-up operation 305, the computer 198, coolant system 106, and the pneumatic air supply 126 may be activated. The warm-up sequence may be initiated by using the control system 124 (e.g., executing an initiation sequence on the computer 198). During the warm-up sequence, the combustion chamber 102 is heated until an equilibrium temperature is reached, for example, about 575 degC.

The method 300 may also include the operation 310 of filtering and preparing the fuel specimen. For example, a user may filter the fuel at room temperature using a glass syringe and a single-use filter element to prepare the fuel, such as about 220 mL or more of the fuel specimen. During operation 315 of the method 300, the reservoir cap 182 (FIG. 1) may be removed from the reservoir body 180 and the reservoir body 180 filled with the fuel. The reservoir cap 182 may then be reinstalled. All of the fuel may be flushed through the fuel injection system until the fuel reservoir 160 is empty. In operation 315, the reservoir cap 182 may then be removed and the reservoir body 180 refilled with the fuel. The reservoir cap 182 may once again be re-installed.

Still referring to FIG. 3, the method 300 may include the operation 325 of initiating automatic determination of combustion characteristics. In operation 325, the determination of the combustion characteristics may be initiated using the computer system 198 or another portion of the control system 124 (FIG. 1). During or after the initiation described in operation 325, a small specimen of fuel may be injected into the heated, temperature-controlled combustion chamber 102, which was previously charged with compressed air. In this embodiment, each injection may produce a single-shot, compression ignition combustion event. Some embodiments of the system 100 may provide for determination of values for combustion characteristics such as ID, MDP, MDT, ROHRA, CP, TAMPD, or the like (described, for example, in connection with FIGS. 4-16).

In operation 330, one or more combustion events in the combustion chamber may be monitored. For example, a user may monitor the combustion event to verify that the injection time period is within an appropriate range, such as between 4.0 ms and 6.0 ms. In some embodiments, a more thorough test sequence may be accomplished by initiating the system 100 to perform two preliminary combustion events and a plurality of consecutive combustion events (e.g., three, five, ten, fifteen, twenty, twenty-five, or more), during which the combustion events are monitored by a user and the sensors transmit data for each of the consecutive events. In those circumstances, the combustion events may be monitored, for example, to verify that the injection period average and the individual injection periods are within an appropriate range, such as an average of 5.00 ms+/−0.25 ms and individual periods between 4.0 ms and 6.0 ms. If either the injection period average or the individual injection periods fall outside of the respective limits, adjustments may be required, such as adjustments to the fuel injector nozzle 162 and the spring-loaded needle extension 164. Following any such adjustments, the method 300 may be repeated starting with the preparation of more fuel 310. If both the injection period average and the individual injection periods fall within the limits, the test may be accepted and the results may be analyzed.

The method 300 may also include the operation 335 of viewing an output report generated by the system 100. In operation 335, the output report 210 may be generated by the computer system 198 and displayed on the display device 200 (refer, for example, to FIG. 2). The output report 210 may include values determined for a plurality of combustion characteristics, such as ID, MDP, MDT, ROHRA, CP, TAMPD, or the like.

In operation 345, the user may exercise an option to compare the output report 210 with one or more output reports 210 of previously tested fuel samples. For example, in operation 350, the user may compare the output reports 210 for one or more of Fuel A, Fuel B, Fuel C, and Fuel D as previously described in connection with FIG. 2. The previously determined values for the combustion characteristics of the tested fuels may be displayed separately or contemporaneously in the multiple-axis plot 212.

In the operation 355, any remaining fuel may be flushed through the fuel injection system 104 until the fuel reservoir 180 is empty. Optionally, the reservoir cap 182 may be removed to visually inspect that the fuel reservoir 180 is empty. The fuel reservoir cap 182 may be reinstalled. In operation 360, the system 100 may again be prepared for a different fuel specimen. Alternatively, the combustion chamber 102 may be shutdown.

If the combustion chamber 102 is to be shutdown, the user may confirm that all fuel has been discharged from the fuel injection system 104 and that the reservoir body 180 is empty. Additionally, the charge air valve 136 at the source of the charge air supply 128 may be closed. In some embodiments, the computer 198 may be used to shutdown the combustion chamber 102. During a complete shutdown, the computer 198, the circulation coolant system 106, and the pneumatic air supply 126 may be turned off, and the combustion chamber 102 may be decompressed and cooled to ambient temperature.

Figure 3B:
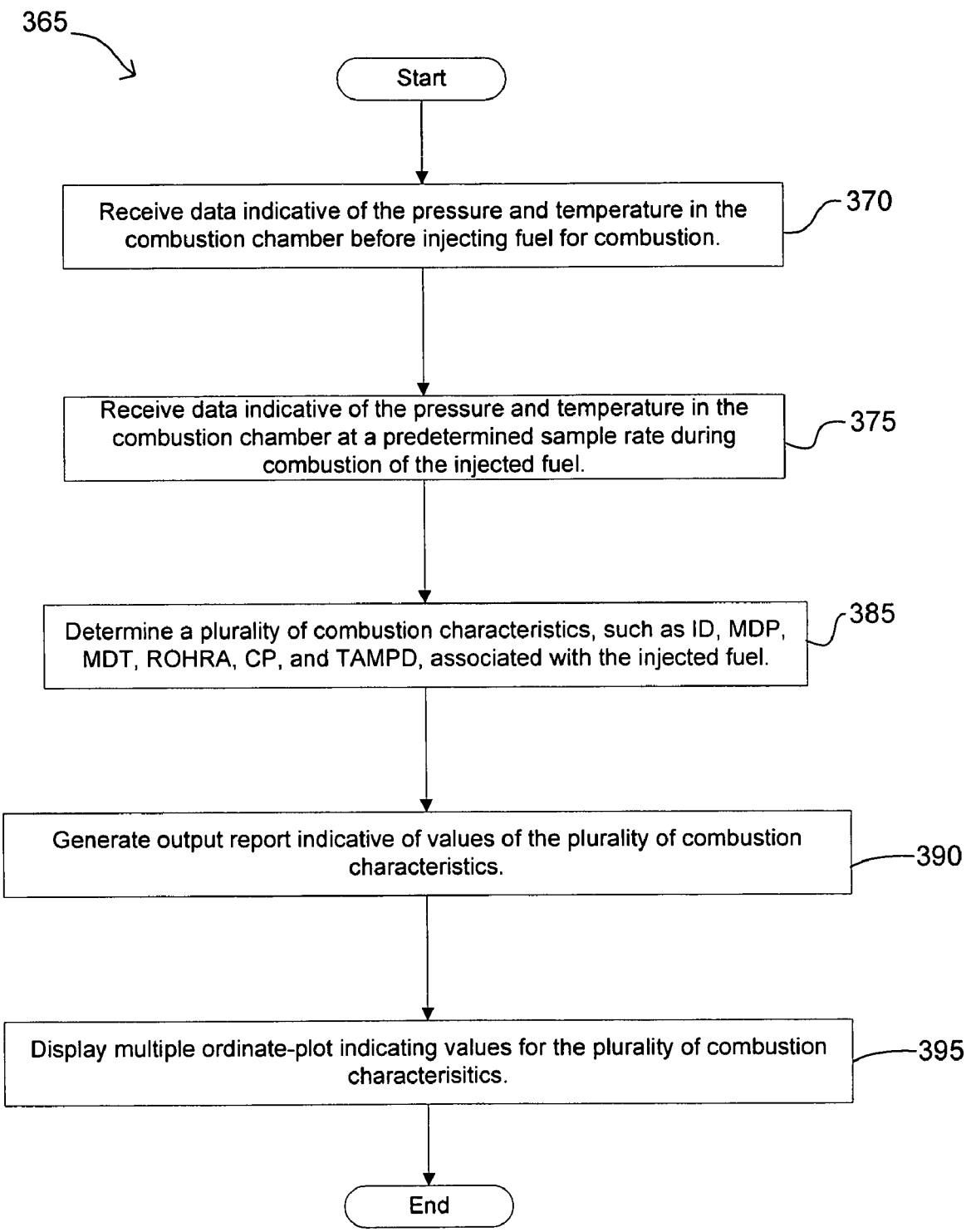
FIG. 3B is a flowchart showing a method for reporting combustion characteristics of a fuel in accordance with some embodiments.

Referring to FIG. 3B, one exemplary method 365 of reporting the combustion characteristics of a tested fuel may include the operation 370 of receiving data indicative of the pressure and temperature in the combustion chamber 102 before the combustion event. As previously described in connection with FIGS. 1-2, the process of determining and reporting combustion characteristics may be at least partially implemented using a computer system, such as computer 198 (FIG. 1). As such, the operation 370 may be at least partially implemented by the computer system 198 receiving one or more data signals from the static pressure sensor 108 and the charge air temperature sensor 116, (e.g., transmitted to the computer system 198 via the control card 194). If both the static pressure and temperature in the combustion chamber are within the appropriate ranges, the combustion chamber 102 may be operational and ready for fuel combustion.

The method 365 may also include the operation 375 of receiving data indicative of the pressure and the temperature in the combustion chamber during the combustion of the fuel. In those embodiments in which operation 375 is at least partially implemented by the computer system 198, the data may be received from the dynamic pressure sensor 100 and the charge air temperature sensor 166. For example, during the one or more combustion events performed while testing a fuel specimen, the dynamic pressure sensor 110 and the charge air temperature sensor 116 may detect the dynamic changes in pressure and temperature at a predetermined sample rate. The computer system 198 may receive one or more data signals from the dynamic pressure sensor 110 and the charge air temperature sensor 116 (e.g., transmitted by the control card 194). In this particular embodiment, the sample rate for receiving data from the dynamic pressure sensor 110 and the charge air temperature sensor 116 may be approximately 0.05 ms and each individual combustion event may occur over a duration of about 100 ms. In other embodiments, different sample rates may be used.

The method 365 may include the operation 385 of determining a plurality of combustion characteristics associated with the injected fuel. In some computer-implemented embodiments, the computer system 198 may include at least one hardware component or a software program stored on the computer memory 208 that is configured to determine (e.g., directly attribute from sensor data, computational algorithm, statistical calculation, mathematical conversion or derivation, other determinative techniques, or a combination thereof) the plurality of combustion characteristics based at least in part on the data received from the sensors. For example, during or after the one or more combustion events, the computer system 198 may determine the values for a plurality of combustion characteristics, such as ID, MDP, MDT, ROHRA, CP, and TAMPD, based at least in part on the data received from the sensors. In this embodiment, the computer system 198 may be adapted to determine the value for ID using pressure and motion data detected via the dynamic pressure sensor 110 and the injector nozzle motion sensor 122. Also in this embodiment, the computer system 198 may be adapted to determine the values for MDP, ROHRA, CP, and TAMPD using pressure data received from the dynamic pressure sensor 110 at the predetermined sample rate. Additionally, in this embodiment, the computer system 198 may be adapted to determine the value for MDT using temperature data detected via the charge air temperature sensor 116 at the sample rate.

The method 365 may also include the operation 390 of generating an output report indicative of the values of the plurality of combustion characteristics. In some computer-implemented embodiments, the computer system 198 may generate an output report (refer, for example, to report 210 described in connection with FIG. 2). For example, the computer memory 208 may comprise a software program that is configured to generate a report (e.g., displayed on the display device 202, printed to a hardcopy, saved to computer memory 208, or a combination thereof) that indicates the values of the combustion characteristics determined in operation 385. In operation 395, the output report may be displayed for viewing by a user. For example, in a computer-implemented embodiment, the output report may be displayed on a display device 202, displayed on a remote display device after transmission over a network, or printed to a hardcopy printout from the computer system 198 or a remote computer system. The output report may include a multiple-axis plot (refer, for example, to plot 212 described in connection with FIG. 2), a pressure trace plot, or both.

As previously described, the method 365 may be at least partially implemented using a computer system. Furthermore, some embodiments of an apparatus or method can be implemented in one or more computer programs that are executable on a computer system including at least one processor. A computer program may be a set of instructions that can be used, directly or indirectly, in a computer system to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment. Also, it should be understood that the components of the computer system can be connected to a medium of digital data communication such as a communication network. Examples of communication networks include, e.g., a LAN, a WAN, and the computers and networks forming the Internet.

Figures 4, 5:
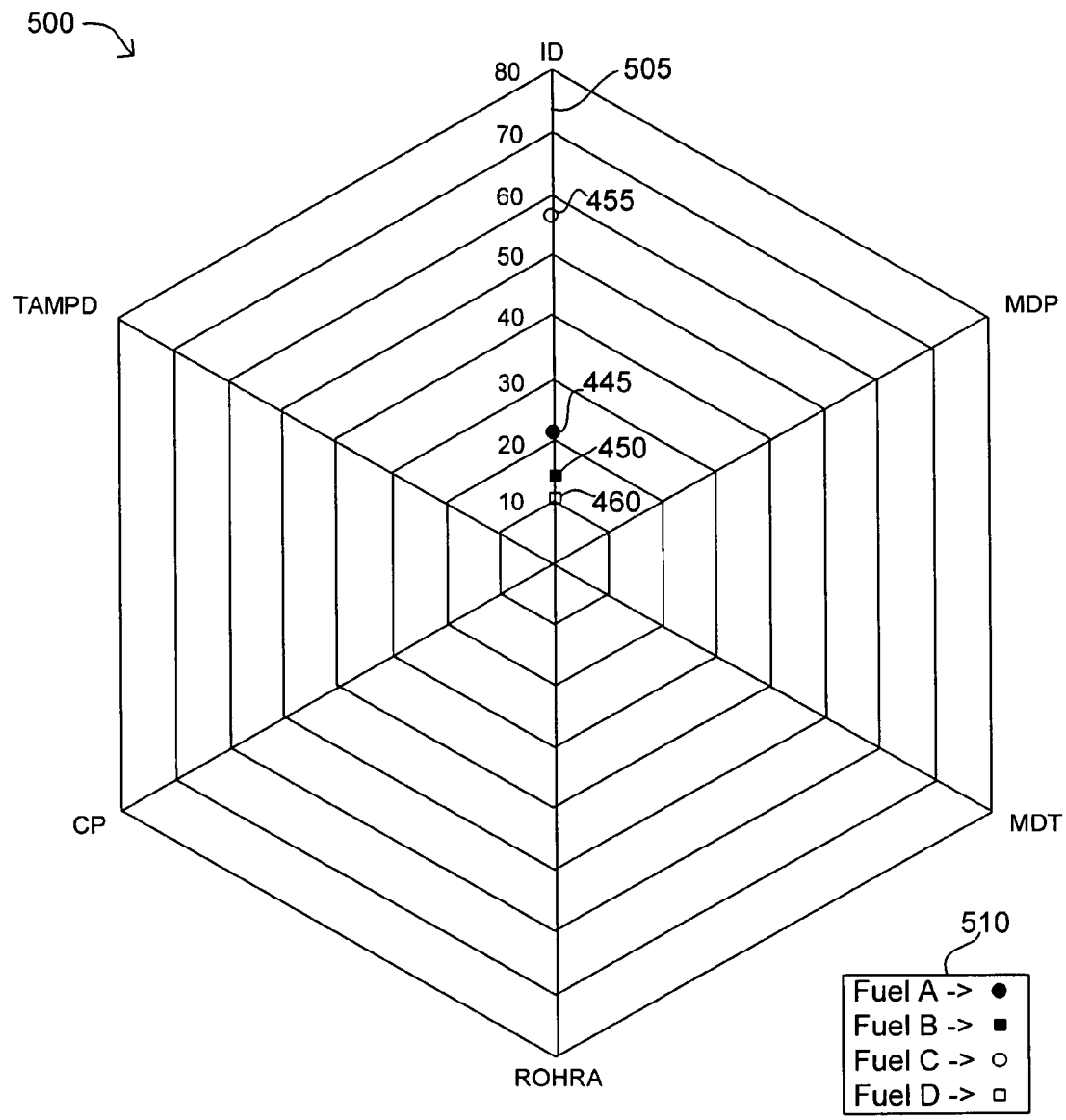
FIG. 4 is an example of a report table for an ignition delay characteristic measured in accordance with some embodiments.
FIG. 5 is an example of a multiple-axis plot showing values for the ignition delay characteristic of FIG. 4.

Referring now to FIGS. 4 and 5, a report table 400 and a multiple-axis plot 500 may be used to display values for the ignition delay (ID) combustion characteristic 405 associated with a plurality of fuels (e.g., fuel A 410, fuel B 415, fuel C 420, and fuel D 425). In some embodiments, the report table 400 and the plot 500 may be displayed, for example, on a computer display device. The report table 400 and the multiple-axis plot 500 may provide for the quantitative and qualitative comparison of the ID values of the different fuels 410, 415, 420, and 425.

As discussed above, the ignition delay combustion characteristic may be defined as the time from the start of injection of the fuel to the start of combustion. The start of combustion is indicated by an increase in combustion chamber pressure over the initial combustion chamber static pressure 234. For practical purposes, the start of combustion can be defined as an increase in combustion chamber pressure above a specified value selected because it clearly indicates the start of combustion. In this particular embodiment, the ignition delay combustion characteristic may be defined as the time from the start of the injection of the fuel to the time that the combustion chamber 102 pressure rises +0.02 MPa above the initial static pressure of 2.4 MPa+/−0.02 MPa. For example, the pressure rise in the combustion chamber 102 may be detected by the dynamic pressure sensor 110, and the start of the injection of the fuel specimen may be detected by the injection nozzle motion sensor 122. It should be understood, that in other embodiments, the ID value may be defined in another manner depending upon the type of sensors used to monitor the combustion event (or events), the settings of the computer software, or other components of the system 100. In some embodiments in which the test sequence comprises a plurality of consecutive combustion events (e.g., twenty-five events in the combustion chamber), the value for the ID characteristic 405 may be obtained by taking the average of the individual ignition delay measurements from the consecutive combustion events. Also, as shown in FIG. 4, the report table 400 may include category 435 to show the measurement unit (e.g., milliseconds) and a category 440 to show a scale conversion value (optionally used to display values in a scaled plot).

The multiple-axis plot 500 may be used to graphically display the values determined for the ID characteristic 405. For example, the values for the ID characteristic 405 may be plotted on the ID axis 505 of the multiple-axis plot 500. In this embodiment, the values may fit in the range of 0.5 ms to 20 ms; therefore, a best-fit scale (refer to category 440) may be employed to associate a 0.5 ms ID value to a scaled value of 0, and 20 ms ID value to a scaled value of 100. It should be understood that, in other embodiments, the scale may be different depending on the viewability of the values in the plot and depending on the sensors and sample rate used in the system 100. The ID values displayed in categories 445, 450, 455, and 460 of the report table 400 show example variations that may occur from one fuel to another. The ID values in this embodiment range from a 2.16 ms value for fuel D 425, to a 3.12 ms value for fuel B 415 and a 4.35 ms value for fuel A 410, and to a 11.5 ms value for fuel C 420. These actually determined values may be displayed in the multiple-axis plot 500, or these values may be converted to scaled values (refer to categories 445, 450, 455, and 460 of report table 400) that are displayed in the plot 500. In this embodiment, the multiple-axis plot 500 displays the scaled values for the ID determination. In some embodiments, the multiple-axis plot 500 may include a legend 510 that associates the tested fuels with a visual identifier (e.g., a unique line, dot, color, or the like).

Figures 6, 7:
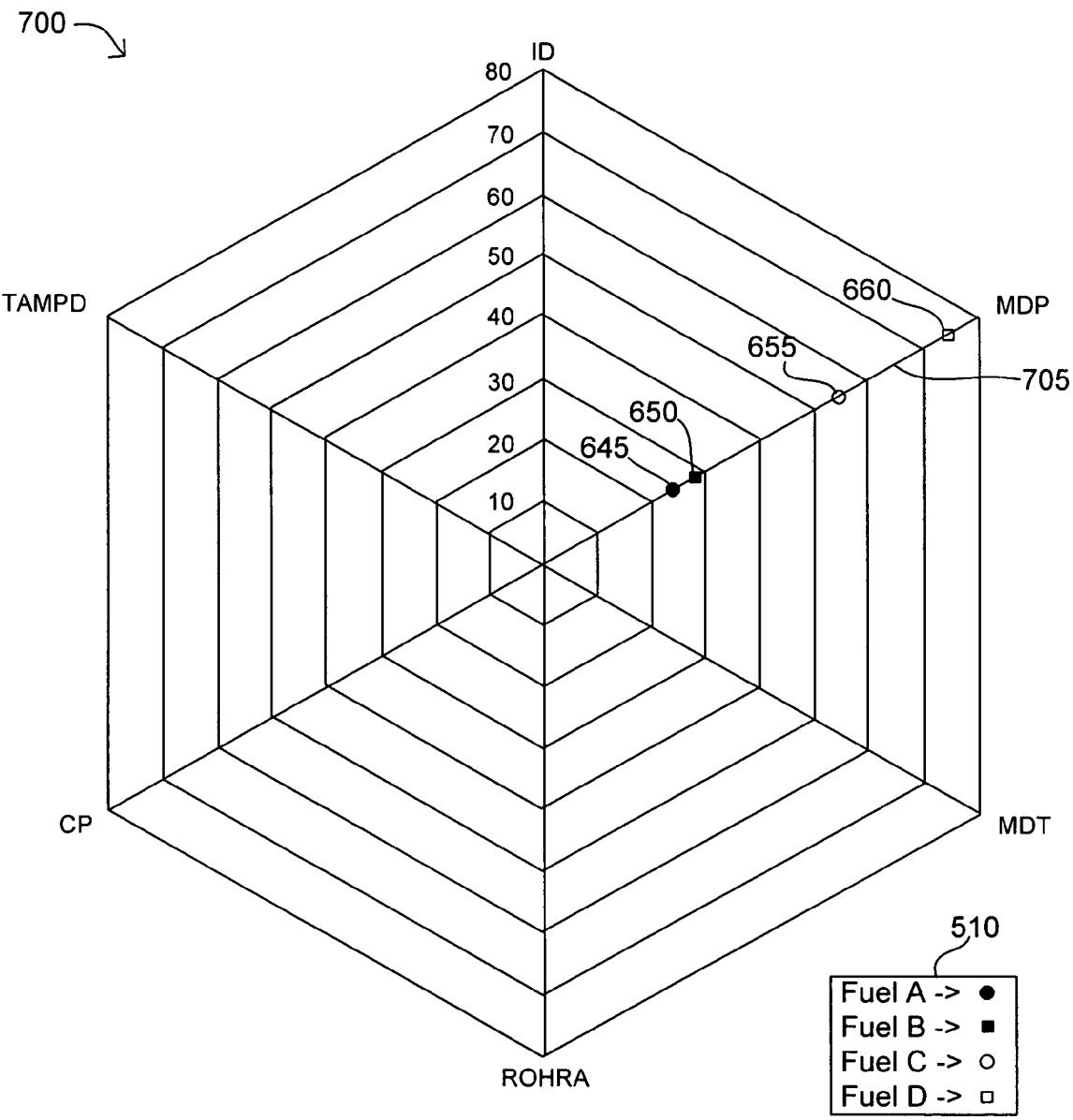
FIG. 6 is an example of a report table for a maximum delta pressure characteristic measured in accordance with some embodiments.
FIG. 7 is an example of a multiple-axis plot showing values for the maximum delta pressure characteristic of FIG. 6.

Referring to FIGS. 6 and 7, a report table 600 and a multiple-axis plot 700 may be used to display values for the maximum delta pressure (MDP) characteristic associated with a plurality of different fuels (e.g., fuel A 410, fuel B 415, fuel C 420, and fuel D 425). As previously described, the report table 600 and the multiple-axis plot 700 may be displayed to a user, for example, on a computer display device. The report table 600 and the multiple-axis plot 700 may provide for the quantitative and qualitative comparison of the MDP values of the different fuels 410, 415, 420, and 425.

In this particular embodiment, the value for the MDP combustion characteristic 605 may be defined as the maximum change in pressure developed during the combustion process (e.g., the maximum pressure developed in the combustion chamber during a particular combustion event minus the static pressure at the beginning of the combustion event). The combustion chamber pressure values during the combustion event may be detected by the dynamic pressure sensor 110. In some embodiments in which the test sequence includes a plurality of consecutive combustion events, the MDP value may be calculated by taking the mean of the individual maximum delta pressure determinations from the consecutive combustion events. The report table 600 may include a category 635 that indicates the unit of measure 635 used for the MDP value, such as bar. It should be understood, that in other embodiments, the MDP value may be defined in another manner depending upon the type of sensors used to monitor the combustion event (or events), the settings of the computer software, or other components of the system 100.

The multiple-axis plot 700 may be used to graphically display the values determined the MDP characteristic 605. For example, the values for the MDP characteristic 605 may be plotted on the MDP axis 705 of the multiple-axis plot according to the legend 510. In this embodiment, the actually determined values may fall in the range of 0 bar to 40 bar. As such, a best-fit scale (refer to category 640) may be used to associate a 0 bar MDP value to a scaled value of 0, and a 40 bar MDP value to a scaled value of 100. It should be understood that, in other embodiments, the scale may be different depending on the viewability of the values in the plot and depending on the sensors and sample rate used in the system 100. The MDP values displayed in categories 645, 650, 655, and 660 of the report table 600 show example variations that may occur among the different fuels. The MDP actual values in this embodiment range from a 9.75 bar value for fuel A 410, to an 11.45 bar value for fuel B 415 and a 22 bar value for fuel C 420, and a 35 bar value for fuel D 425. In this embodiment, the multiple-axis plot 700 displays the scaled values for the MDP determination (refer to the scaled values in categories 645, 650, 655, and 660 of the report 600), but in some embodiments the multiple-axis plot 700 may display the actually determined values as shown in the report table 600.

Figures 8, 9:
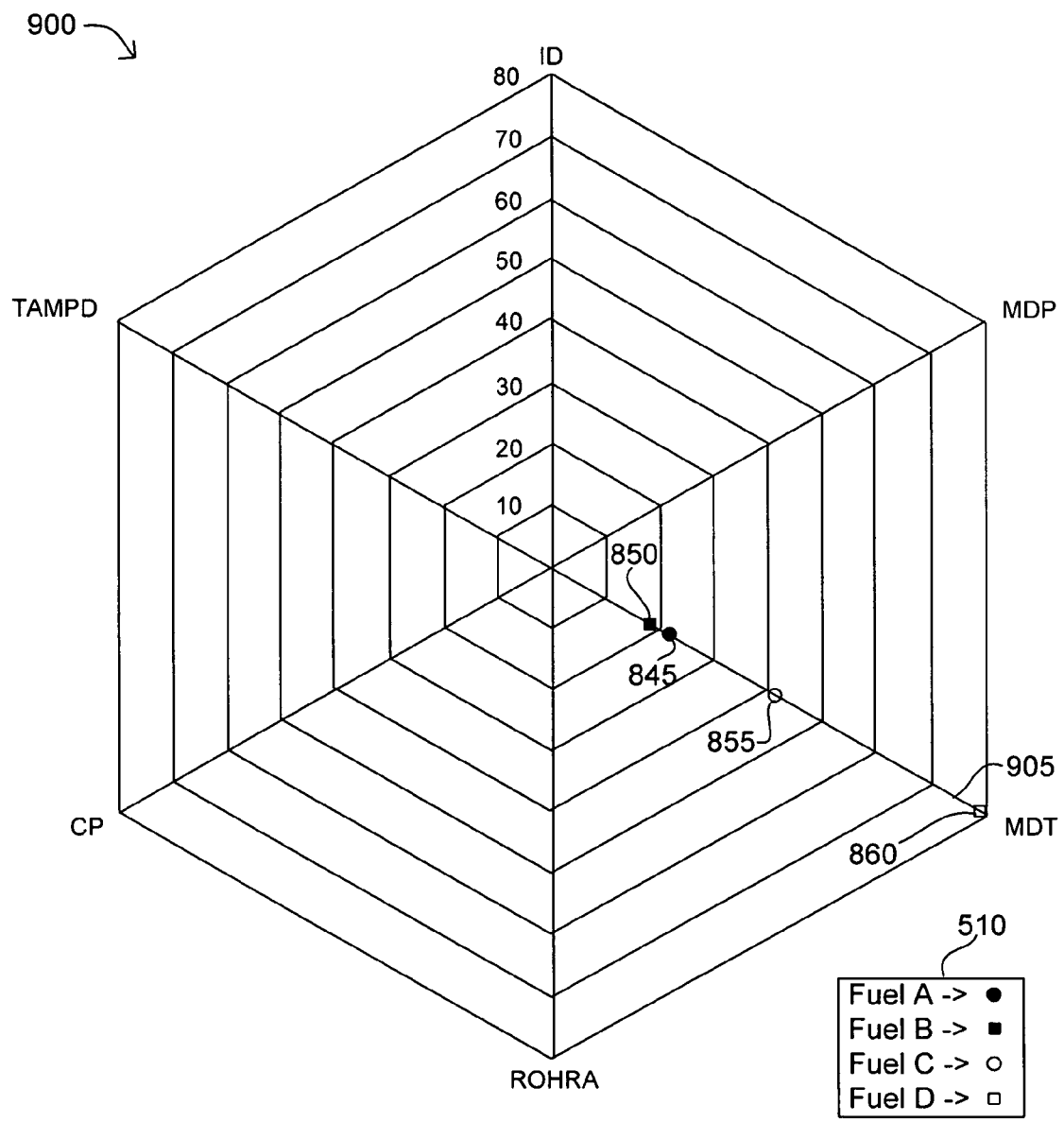
FIG. 8 is an example of a report table for a maximum delta temperature characteristic measured in accordance with some embodiments.
FIG. 9 is an example of a multiple-axis plot showing values for the maximum delta temperature characteristic of FIG. 8.

Referring to FIGS. 8 and 9, a report table 800 and a multiple-axis plot 900 may be used to display values for the maximum delta temperature (MDT) characteristic associated with a plurality of different fuels (e.g., fuel A 410, fuel B 415, fuel C 420, and fuel D 425). In some embodiments, the report table 800 and the multiple-axis plot 900 may be displayed on a computer display device and may provide for the quantitative and qualitative comparison of the MDT values of the different fuels 410, 415, 420, and 425. The report table 800 may include a category 835 that indicates the unit of measure used for the MDT value, such as degrees C. The value for the MDT combustion characteristic 805 may be defined as the maximum change in temperature developed during the combustion process (e.g., the maximum temperature measured in the combustion chamber during a particular combustion event minus the initial temperature at the beginning of the combustion event). It should be understood, that in other embodiments, the MDT value may be defined in another manner depending upon the type of sensors used to monitor the combustion event (or events), the settings of the computer software, or other components of the system 100. The multiple-axis plot 900 may be used to graphically display values (e.g., scaled values or actually determined values) for the MDT characteristic 805. For example, the scaled values for MDT may be plotted on the MDT axis 905 according to the legend 510 and the best-fit scale (refer to category 840 in the report table 800). In this embodiment, the multiple-axis plot 900 displays the scaled values for the MDT determination (refer to the scaled values in categories 845, 850, 855, and 860 of the report 800), but in some embodiments the multiple-axis plot 900 may display the actually determined values as shown in the report table 800.

Figures 10, 11:
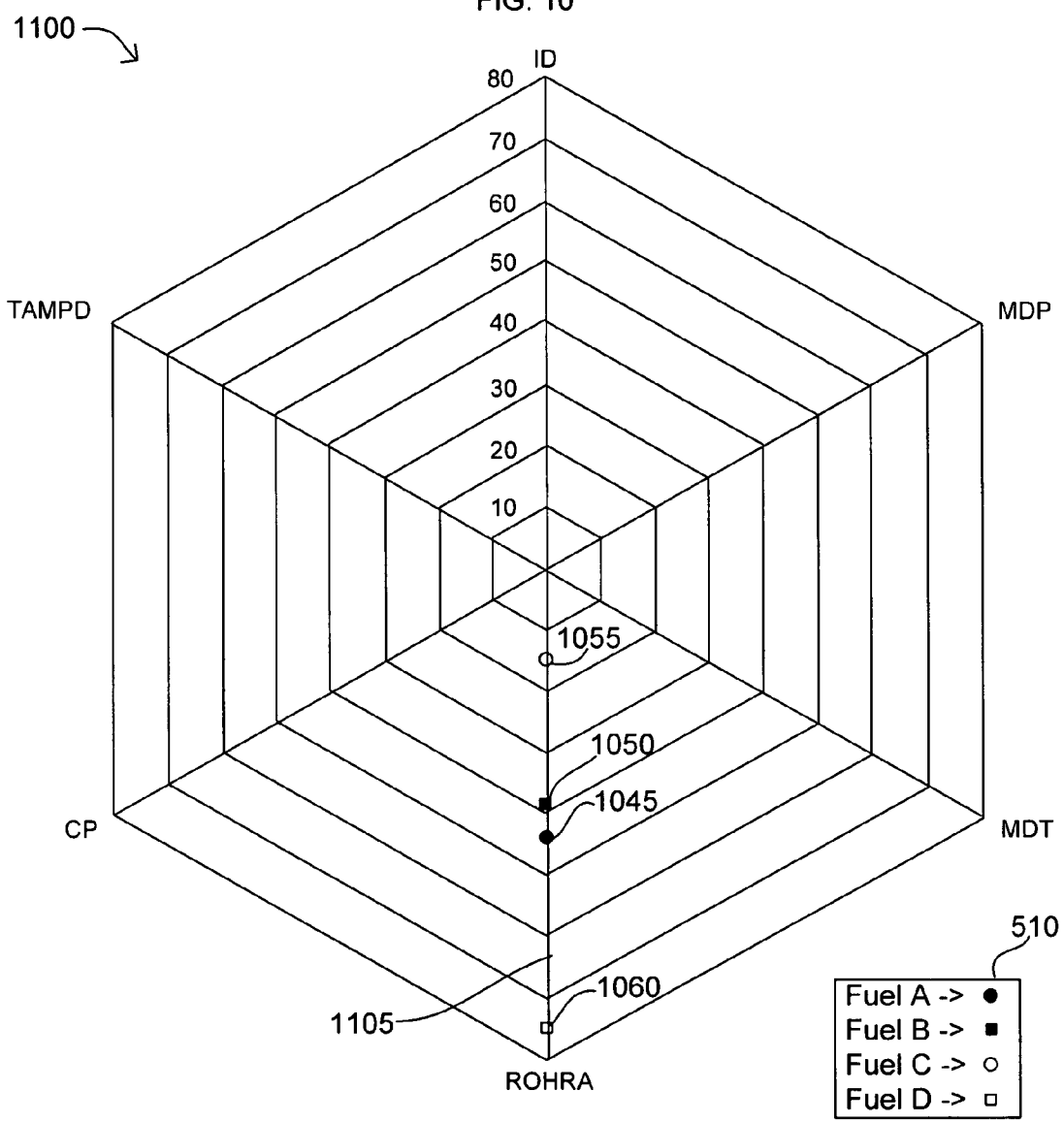
FIG. 10 is an example of a report table for a rate of heat release area characteristic measured in accordance with some embodiments.
FIG. 11 is an example of a multiple-axis plot showing values for the rate of heat release area characteristic of FIG. 10.

Referring to FIGS. 10 and 11, a report table 1000 and a multiple-axis plot 1100 may be used to display values for the rate of heat release area (ROHRA) characteristic associated with a plurality of different fuels (e.g., fuel A 410, fuel B 415, fuel C 420, and fuel D 425). In some embodiments, the report table 1000 and the multiple-axis plot 1100 may be displayed on a computer display device and may provide for the quantitative and qualitative comparison of the ROHRA values of the different fuels 410, 415, 420, and 425. The report table 1000 may include a category 1035 that indicates the unit of measure used for the ROHRA value, such as Bar/ms$^2$. In this embodiment, the value for the ROHRA combustion characteristic 1005 may be defined as the maximum change in temperature developed during the combustion process (e.g., may be determined by calculation of the area under the curve of the derivative of the pressure trace). It should be understood, that in other embodiments, the ROHRA value may be defined in another manner depending upon the type of sensors used to monitor the combustion event (or events), the settings of the computer software, or other components of the system 100. The multiple-axis plot 1100 may be used to graphically display values (e.g., scaled values or actually determined values) for the ROHRA characteristic 1005. For example, the scaled values for ROHRA may be plotted on the ROHRA axis 1105 according to the legend 510 and the best-fit scale (refer to category 1040 in the report table 1000). In this embodiment, the multiple-axis plot 1100 displays the scaled values for the ROHRA determination (refer to the scaled values in categories 1045, 1050, 1055, and 1060 of the report 1000), but in some embodiments the multiple-axis plot 1100 may display the actually determined values as shown in the report table 1000.

Figures 12, 13:
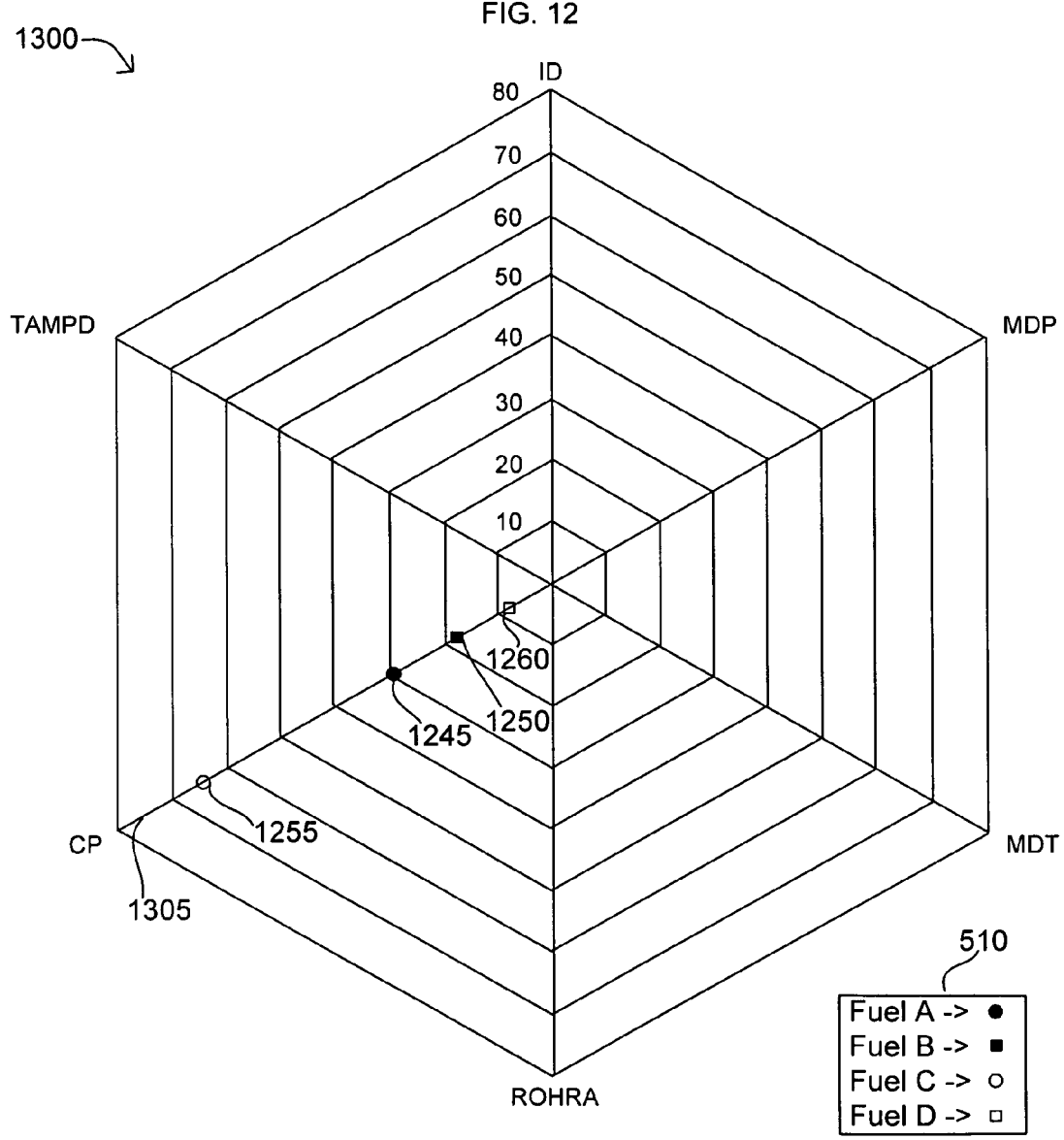
FIG. 12 is an example of a report table for a combustion period characteristic measured in accordance with some embodiments.
FIG. 13 is an example of a multiple-axis plot showing values for the combustion period characteristic of FIG. 12.

Referring to FIGS. 12 and 13, a report table 1200 and a multiple-axis plot 1300 may be used to display values for the combustion period (CP) characteristic associated with a plurality of different fuels (e.g., fuel A 410, fuel B 415, fuel C 420, and fuel D 425). In some embodiments, the report table 1200 and the multiple-axis plot 1300 may be displayed on a computer display device and may provide for the quantitative and qualitative comparison of the CP values of the different fuels 410, 415, 420, and 425. The report table 1200 may include a category 1235 that indicates the unit of measure used for the CP value, such as milliseconds. The value for the CP combustion characteristic 1205 may be defined as the duration in time of the combustion event. For practical purposes, the combustion event can be defined as occurring when the sustained increase in pressure due to combustion is over a specified value. In this embodiment, the combustion event is defined as occurring when the sustained increase in pressure do to combustion is over 0.05 bar/ms$^2$. It should be understood, that in other embodiments, the CP value may be defined in another manner depending upon the type of sensors used to monitor the combustion event (or events), the settings of the computer software, or other components of the system 100. The multiple-axis plot 1300 may be used to graphically display values (e.g., scaled values or actually determined values) for the CP characteristic 1205. For example, the scaled values for CP may be plotted on the CP axis 1305 according to the legend 510 and the best-fit scale (refer to category 1240 in the report table 1200). In this embodiment, the multiple-axis plot 1300 displays the scaled values for the CP determination (refer to the scaled values in categories 1245, 1250, 1255, and 1260 of the report 1200), but in some embodiments the multiple-axis plot 1300 may display the actually determined values as shown in the report table 1200.

Figures 14, 15:
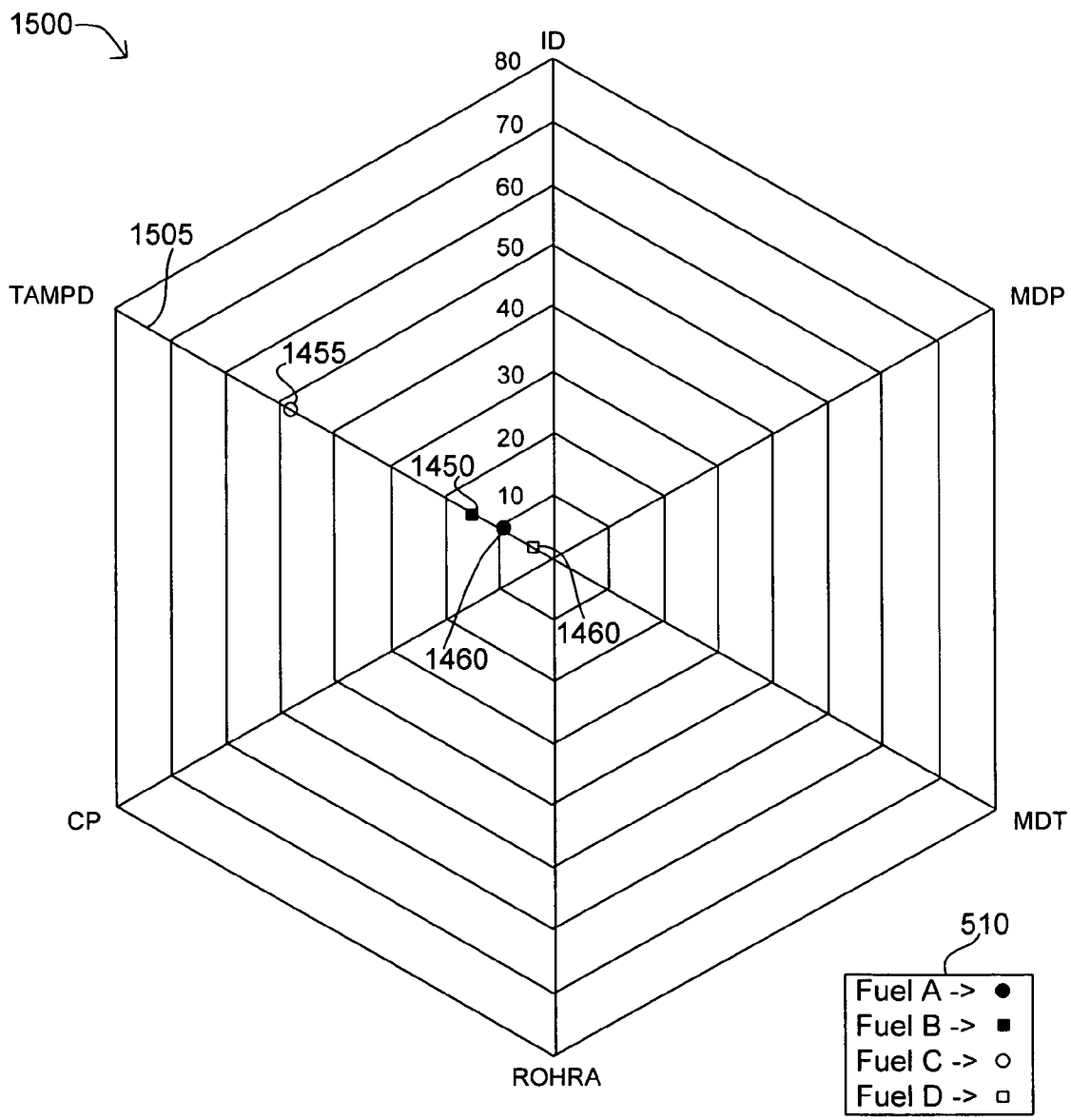
FIG. 14 is an example of a report table for the time at maximum pressure developed characteristic measured in accordance with some embodiments.
FIG. 15 is an example of a multiple-axis plot showing values for the time at maximum pressure developed characteristic of FIG. 14.

Referring to FIGS. 14 and 15, a report table 1400 and a multiple-axis plot 1500 may be used to display values for the time at maximum pressure detected (TAMPD) characteristic associated with a plurality of different fuels (e.g., fuel A 410, fuel B 415, fuel C 420, and fuel D 425). In some embodiments, the report table 1400 and the multiple-axis plot 1500 may be displayed on a computer display device and may provide for the quantitative and qualitative comparison of the TAMPD values of the different fuels 410, 415, 420, and 425. The report table 1400 may include a category 1435 that indicates the unit of measure used for the TAMPD value, such as milliseconds. The value for the TAMPD combustion characteristic 1405 may be defined as the duration in time from the start of combustion (e.g. the start of combustion used in determining the ignition delay combustion characteristic 405 to the maximum combustion pressure. It should be understood, that in other embodiments, the TAMPD value may be defined in another manner depending upon the type of sensors used to monitor the combustion event (or events), the settings of the computer software, or other components of the system 100. The multiple-axis plot 1500 may be used to graphically display values (e.g., scaled values or actually determined values) for the TAMPD characteristic 1405. For example, the scaled values for TAMPD may be plotted on the TAMPD axis 1505 according to the legend 510 and the best-fit scale (refer to category 1440 in the report table 1400). In this embodiment, the multiple-axis plot 1500 displays the scaled values for the TAMPD determination (refer to the scaled values in categories 1445, 1450, 1455, and 1460 of the report 1400), but in some embodiments the multiple-axis plot 1500 may display the actually determined values as shown in the report table 1400.

Figure 16:
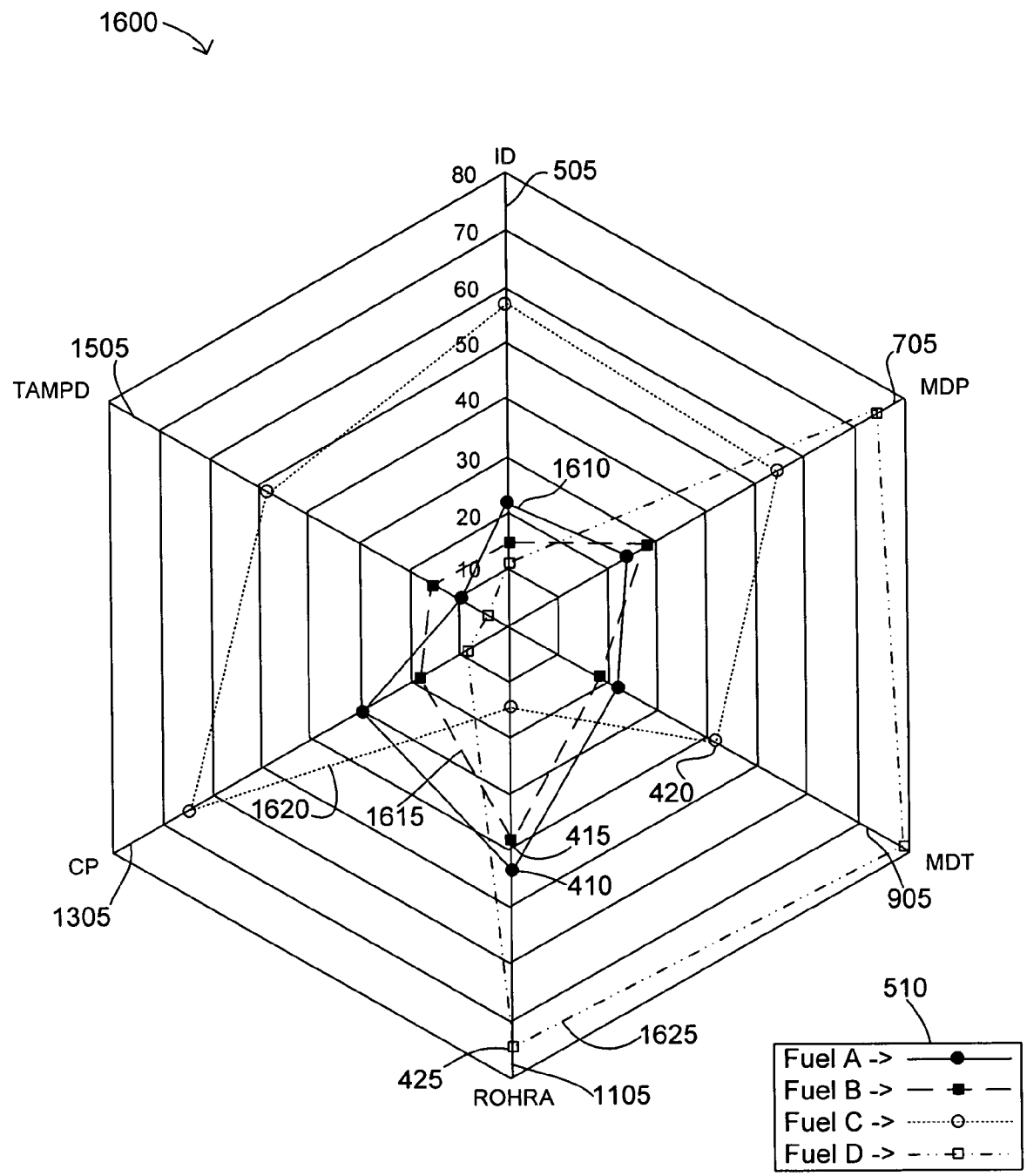
FIG. 16 is an example of a multiple-axis plot that may be used as a fuel form factor in accordance with some embodiments.

Referring to FIG. 16, a multiple-axis plot 1600 may serve as a fuel form factor. The plot 1600 may provide a model for efficient comparison and analysis of combustion characteristics, for example, some or all of the previously described ID, MDP, MDT, ROHRA, CP, and TAMPD characteristics and other characteristics (e.g. octante number, cetane number, aromatic content or the like. The combustion characteristic values for a plurality of different fuels (e.g., fuel A 410, fuel B 415, fuel C 420, and fuel D 425) may be contemporaneously displayed on the multiple-axis plot 1600 to provide an efficient comparison and analysis tool. In some embodiments, the fuel form factor displayed in the multiple-axis plot 1600 may be used to assess the suitability of the tested fuel for operation in a particular engine configuration.

The plot 1600 may be created in a manner similar to the multiple-axis plots 500, 700, 900, 1100, 1300, and 1500 described in connection with FIGS. 5, 7, 9, 11, 13, and 15. In some circumstances, lines 1610, 1615, 1620, and 1625 may be drawn connecting the combustion characteristic values associated with each of the four diesel fuels 410, 415, 420, and 425, thereby providing a shape that may be different for each of the different fuels. As previously described in connection with FIGS. 2, 3A, and 3B, the multiple-axis plot 1600 may be generated for viewing by a user after the one or more combustion events are performed within the combustion chamber 102 (FIG. 1). The user is then permitted to contemporaneously analyze a plurality of combustion characteristics for different fuels of interest. By serving as a form factor, the multiple-axis plot 1600 may provide an efficient tool to compare various characteristics of tested fuels. It should be understood that that, in some embodiments, the fuel form factor may be at least partially defined by the shape of the multiple-axis plot. In other embodiments, the fuel form factor may be at least partially defined by an area value of the shape of the multiple-axis plot such that different fuels may be distinguished by the different area values at particular ordinates.

In some embodiments, the resultant fuel form factor may provide an engine designer with a method of comparing the fuel performance characteristics of an engine at a given condition. For example, if an engine design performs better with fuel A 410 at a first temperature and then performs better with fuel D 425 at a second temperature, the engine designer may view the form factor displayed on the multiple-axis plot 1600 so as to quantitatively or qualitatively compare the characteristics of fuel A 410 to fuel D 425. Such a tool may permit the engine designer or other user to develop an alternate fuel mixture that satisfactorily performs at both the first and second temperatures. The alternate fuel mixture, for example fuel B 415, may provide a suitable compromise of the combustion characteristics (e.g., ID, MDP, MDT, ROHRA, CP, TAMPD, or other characteristics determined by the system 100) that fuel A 410 and fuel D 425 did not provide in this case. Such a comparison of fuel characteristics may be implemented as part of systems and methods as described, for example, in connection with FIGS. 1, 2, and 3A-B.

For example, in particular embodiments, the multiple-axis plot 1600 may serve as a fuel form factor to select commercially feasible fuels for use in a particular engine design. In this example, a user may test fuel A in a particular engine and determine that fuel A provides desirable combustion characteristics. If fuel A is an expensive test fuel, the wide-scale commercial use of fuel A in the engine design may be impracticable. In such circumstances, the user may compare the form factor of fuel A 1610 (shown in the multiple-axis plot 1600) to form factors of other fuels to see if a less expensive fuel provides similar combustion characteristics. In this example, the user may select fuel B based at least in part on a comparison of the shape of the form factors 1610 and 1615. Fuel B may be a blend of less expensive, more readily available commercial fuels or a commercial fuel blend with additional additives that cause combustion characteristics similar to the tested fuel A. Through this process, a user or group of users may populate a database (e.g., stored in the computer memory 208 (FIG. 2) and accessible via the display device 208) which has fuel form factors for each type of fuel. Thus, the system 100 may be used to develop a comprehensive database that shows correlations between the fuel form factor shapes for a number of fuels and the combustion results of those fuels in a particular engine design. In addition, such a database may be used by combustion modeling software to directly input the fuel form factor shape into an additional module of the combustion modeling software, thereby eliminating iterations of fuel combustion characteristics. It should be understood that a user test the different fuels in an engine simulation system rather than in an actual combustion engine. For example, data from the multiple-axis plot may be input into an engine simulation system (e.g., GT-Power engine simulation software system, CFD (computational fluid dynamics) modeling and simulation software system, Matlab simulation modules, and other simulation systems implemented on a computer system or the like) to provide feedback for certain criteria of the fuel's combustion characteristics. Accordingly, the data from the multiple-axis plot may facilitate the custom fuel design or selection by permitting a designer to readily simulate the combustion of one or more fuels in a simulated engine using the engine simulation system.

Still referring to FIG. 16, in other embodiments, the fuel form factor displayed in the multiple-axis plot 1600 may provide an engine designer with a method for altering an engine design based upon a comparison of fuel characteristics. In one example, the engine designer may compare and analyze the combustion characteristics of fuel A 410 and fuel C 420. If the engine's current design performs better with fuel A 410 (even though fuel C 420 is supposed to be used for commercial reasons or other reasons), the form factor shapes displayed on the plot 1600 may indicate which characteristic is affecting the performance of fuel C 420. Such a quantitatively or qualitatively comparison may cause the designer or other user to alter the design of the engine to better accommodate fuel C 420. For example, the engine designer may be prompted to alter the compression ratio, the piston dome design, the cylinder head combustion chamber shape, the bore and stroke, or the camshaft lift and duration based on the combustion characteristics 405, 605, 805, 1005, 1205, and 1405 of fuel C 420.

For example, in particular embodiments, some engine designs (e.g., HCCI or the like) may require a fuel that auto-ignites readily at low load or cold conditions but ignites less easily at higher load conditions. In such circumstance, a user may test the same fuel in the combustion chamber 102 of the system 100 under both low load conditions and high load conditions. By evaluating the fuel form factor (shown in the multiple-axis plot 1600) for the tested fuel at both low load condition and high load conditions, the user may identify a fuel that has suitable auto-ignition characteristics at the low load conditions and the high load conditions. Alternatively, by evaluating the fuel form factor (shown in the multiple-axis plot 1600) for the tested fuel at both low load condition and high load conditions, the user may determine that the fuel has a suitable resistance to auto-ignition at the high load conditions (e.g., greater ignition delay) and may then quantify how much the ignition delay should be reduced at the lower load conditions. In such circumstances, the user may adjust the engine design or other features to accommodate the use of the tested fuel. For example, user may employ an algorithm in the engine's control system that would change the amount of turbulence (or swirl ratio) at the lower load conditions, which may reduce the ignition delay at the lower load conditions. As previously described, it should be understood that a user may test a particular fuel in a number of simulated engines rather than in an actual combustion engine. For example, data from the multiple-axis plot may be input into an engine simulation system (e.g., GT-Power engine simulation software system, CFD (computational fluid dynamics) modeling and simulation software system, Matlab simulation modules, and other simulation systems implemented on a computer system or the like) to provide feedback for certain criteria of the fuel's combustion characteristics. As such, the data from the multiple-axis plot may facilitate the engine design by permitting a designer to readily simulate the combustion of the particular fuel in a number of simulated engine designs using the engine simulation system.

A number of embodiments of the invention have been described. Nevertheless, it will be understood that various modifications may be made without departing from the spirit and scope of the invention. Accordingly, other embodiments are within the scope of the following claims.

What is claimed is:

1. A method for determining the operability of a fuel in an engine, said method comprising:
identifying values for at least three combustion characteristics of a tested fuel selected from the group consisting of ignition delay, maximum delta pressure, maximum delta temperature, rate of heat release area, combustion period, and time at which the maximum pressure developed;
using the identified values to assess the suitability of the tested fuel for operation in an engine configuration.

2. The method of claim 1, wherein the plurality of combustion characteristics includes at least the group of characteristics consisting of ignition delay, maximum delta pressure, maximum delta temperature, rate of heat release area, combustion period, and time at which the maximum pressure developed.

3. The method of claim 1, wherein at least one of the values of the combustion characteristics is automatically identified by a computer system.

4. The method of claim 1, wherein using the identified values to assess the suitability of the tested fuel comprises evaluating an output report that identifies the fuel and is indicative of determined or scaled values of the at least three combustion characteristics.

5. The method of claim 4, wherein the output report includes the determined or scaled values of the at least three combustion characteristics displayed on a multiple-axis plot, the multiple-axis plot having an axis for each of the at least three combustion characteristics.

6. A method for assessing combustion characteristics of a fuel, said method comprising:
determining values for at least three combustion characteristics of a fuel selected from the group consisting of ignition delay, maximum delta pressure, maximum delta temperature, rate of heat release area, combustion period, and time at which the maximum pressure developed;
associating the determined values with the fuel.

7. The method of claim 6, wherein the plurality of combustion characteristics includes at least the group of characteristics consisting of ignition delay, maximum delta pressure, maximum delta temperature, rate of heat release area, combustion period, and time at which the maximum pressure developed.

8. The method of claim 6, wherein the values for the at least three combustion characteristics are determined based at least partially upon data indicative of pressure, temperature, or both in a combustion chamber measured at a predetermined sample rate of 0.2 ms or less during combustion of the fuel in the combustion chamber.

9. The method of claim 6, wherein at least one of the values of the combustion characteristics is automatically determined by a computer system.

10. The method of claim 6, wherein the determined values are associated with the fuel in an output report that identifies the fuel and is indicative of determined or scaled values of the at least three combustion characteristics.

11. The method of claim 10, wherein the output report includes the determined or scaled values of the at least three combustion characteristics displayed on a multiple-axis plot, the multiple-axis plot having an axis for each of the at least three combustion characteristics.

12. A method for assessing a combustion characteristic of a fuel, said method comprising:
determining a value for at least one combustion characteristic of a fuel selected from the group consisting of rate of heat release area and combustion period;
associating the determined value with the fuel.

13. The method of claim 12, further comprising determining a value for at least one combustion characteristic selected from the group consisting of ignition delay, maximum delta pressure, maximum delta temperature, and time at which the maximum pressure developed.

14. The method of claim 12, wherein the value for the at least one combustion characteristic is determined based at least partially upon data indicative of pressure, temperature, or both in a combustion chamber measured at a predetermined sample rate of during combustion of the fuel in the combustion chamber.

15. The method of claim 13, wherein the predetermined sample rate is 0.2 ms or less.

16. The method of claim 12, wherein at least one of the values of the combustion characteristics is automatically determined by a computer system.

17. A computer-implemented method of reporting combustion characteristics of a fuel, comprising:
receiving data indicative of pressure and temperature in a combustion chamber at a predetermined sample rate during combustion of a fuel in the combustion chamber;
determining values for a plurality of combustion characteristics associated with the fuel combusted in the combustion chamber, the plurality of combustion characteristics being at least three of the characteristics selected from the group consisting of: ignition delay, maximum delta pressure, maximum delta temperature, rate of heat release area, combustion period, and time at which the maximum pressure developed; and
generating an output report indicative of determined or scaled values of the at least three combustion characteristics, the output report including the determined or scaled values of the at least three combustion characteristics displayed on a multiple-axis plot, the multiple-axis plot having an axis for each of the at least three combustion characteristics.

18. The method of claim 17, wherein the plurality of combustion characteristics includes at least the group of characteristics consisting of ignition delay, maximum delta pressure, maximum delta temperature, rate of heat release area, combustion period, and time at which the maximum pressure developed.

19. The method of claim 17, wherein the data indicative of pressure in a combustion chamber during combustion of the fuel is received from at least one dynamic pressure sensor at a sample rate of 0.2 ms or less.

20. The method of claim 17, wherein the output report includes a list of the determined values of the at least three combustion characteristics, the list being displayed contemporaneously with the multiple-axis plot.

21. The method of claim 20, wherein the output report includes a pressure trace plot indicative of the pressure in the combustion chamber before and during combustion of the fuel, the pressure trace plot being displayed contemporaneously with the multiple-axis plot.

22. The method of claim 17, further comprising receiving data indicative of pressure and temperature in a combustion chamber before the combustion of the fuel in the combustion chamber.

23. A method of identifying combustion characteristics of a fuel, comprising:
    initiating a computer system to determine values for a plurality of combustion characteristics associated with a first fuel combusted in the combustion chamber, the plurality of combustion characteristics being at least three of the characteristics selected from the group consisting of: ignition delay, maximum combustion pressure, maximum combustion temperature, rate of heat release, combustion period, and time at which the maximum pressure developed;
    causing the first fuel to be injected into a combustion chamber so that the first fuel combusts, the combustion chamber including one or more sensors that are electrically coupled to the computer system;
    viewing an output report generated by the computer system indicative of determined or scaled values of the at least three combustion characteristics, the output report including a multiple-axis plot having an axis for each of the at least three combustion characteristics.

24. The method of claim 23, wherein the plurality of combustion characteristics includes at least the group of characteristics consisting of ignition delay, maximum combustion pressure, maximum combustion temperature, rate of heat release, combustion period, and time at which the maximum pressure developed.

25. The method of claim 23, wherein at least one of the values of the combustion characteristics is automatically determined based upon a data received from the one or more sensors during combustion of the fuel, the data being indicative of pressure and temperature in the combustion chamber.

26. The method of claim 23, wherein the output report contemporaneously indicates first values of combustion characteristics associated with the first fuel and second values of combustion characteristics associated with a second fuel.

27. The method of claim 26, wherein the first values and the second values are contemporaneously displayed on the multiple-axis plot.

* * * * *

UNITED STATES PATENT AND TRADEMARK OFFICE
CERTIFICATE OF CORRECTION

PATENT NO. : 7,529,616 B2 Page 1 of 1
APPLICATION NO. : 11/390942
DATED : May 5, 2009
INVENTOR(S) : Jeffrey Jacob Bizub It is certified that error appears in the above-identified patent and that said Letters Patent is hereby corrected as shown below:

In sheet 4 of drawings, figure 3B, reference numeral 395 – replace "characterisitics" with -- characteristics --

In column 16, fine 63 – replace "octante" with -- octane --

Signed and Sealed this

Twenty-third Day of June, 2009

JOHN DOLL
*Acting Director of the United States Patent and Trademark Office*